(12) United States Patent
Triplett et al.

(10) Patent No.: US 8,628,576 B2
(45) Date of Patent: Jan. 14, 2014

(54) EXPANDABLE INTERVERTEBRAL IMPLANTS AND INSTRUMENTS

(75) Inventors: Daniel J. Triplett, Providence, UT (US); Joshua A. Butters, Chandler, AZ (US); Nicholas Slater, Chandler, AZ (US); Cortny Robison, Salt Lake City, UT (US)

(73) Assignee: IMDS Corporation, Providence, UT (US)

( * ) Notice: Subject to any disclaimer, the term of this patent is extended or adjusted under 35 U.S.C. 154(b) by 0 days.

(21) Appl. No.: 13/396,287

(22) Filed: Feb. 14, 2012

(65) Prior Publication Data

US 2012/0209386 A1 Aug. 16, 2012

Related U.S. Application Data

(60) Provisional application No. 61/442,482, filed on Feb. 14, 2011, provisional application No. 61/554,374, filed on Nov. 1, 2011.

(51) Int. Cl.
*A61F 2/44* (2006.01)

(52) U.S. Cl.
USPC ..................... 623/17.11; 623/17.13

(58) Field of Classification Search
USPC ........ 623/17.11–17.16; 606/279, 86 A, 86 B, 606/99
See application file for complete search history.

(56) References Cited

U.S. PATENT DOCUMENTS

| | | | |
|---|---|---|---|
| 4,164,225 A | 8/1979 | Johnson | |
| 5,171,278 A | 12/1992 | Pisharodi | |
| 5,693,100 A | 12/1997 | Pisharodi | |
| 6,039,761 A | 3/2000 | Li | |
| 2006/0142858 A1* | 6/2006 | Colleran et al. | 623/17.11 |
| 2006/0241643 A1 | 10/2006 | Lim | |
| 2007/0118222 A1 | 5/2007 | Lang | |
| 2008/0243255 A1* | 10/2008 | Butler et al. | 623/17.16 |
| 2009/0076607 A1 | 3/2009 | Aalsma | |
| 2009/0157084 A1 | 6/2009 | Aalsma | |
| 2010/0174373 A1* | 7/2010 | Galley et al. | 623/17.13 |
| 2011/0282453 A1* | 11/2011 | Greenhalgh et al. | 623/17.16 |
| 2012/0004732 A1* | 1/2012 | Goel et al. | 623/17.16 |
| 2012/0123546 A1* | 5/2012 | Medina | 623/17.16 |
| 2012/0185047 A1* | 7/2012 | Wooley | 623/17.16 |

FOREIGN PATENT DOCUMENTS

| | | |
|---|---|---|
| WO | WO0025706 | 5/2000 |
| WO | WO2008070863 | 6/2008 |
| WO | WO2010078468 | 7/2010 |
| WO | WO2010105181 | 9/2010 |

* cited by examiner

*Primary Examiner* — Pedro Philogene
*Assistant Examiner* — Lynnsy Schneider
(74) *Attorney, Agent, or Firm* — G. Jo Hays; James Larson; James M. Pinkston

(57) ABSTRACT

Systems for interbody fusion of adjacent bone portions may include an expanding implant and related instruments. An expanding implant may be formed as a linkage which is movable between a compact configuration and an expanded configuration. A shaft of the implant may increase and decrease in length to move between the compact and expanded configurations, and an implant width perpendicular to the length may be increased in the expanded configuration. The implant width may increase more in a first direction than a second direction opposite the first direction. An inserter instrument may releasably grasp the spacer and transform the implant between the compact and expanded configurations.

20 Claims, 17 Drawing Sheets

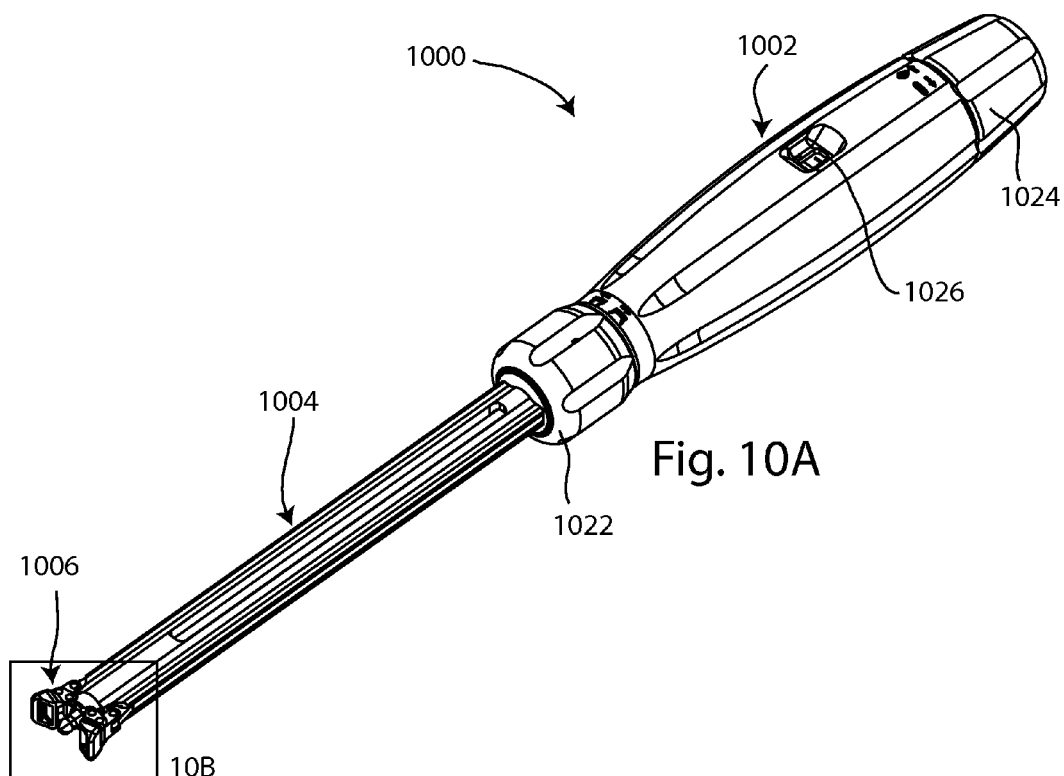
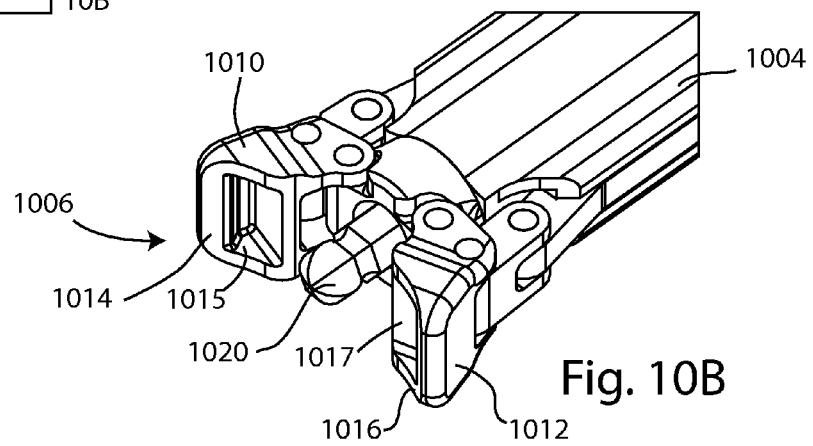

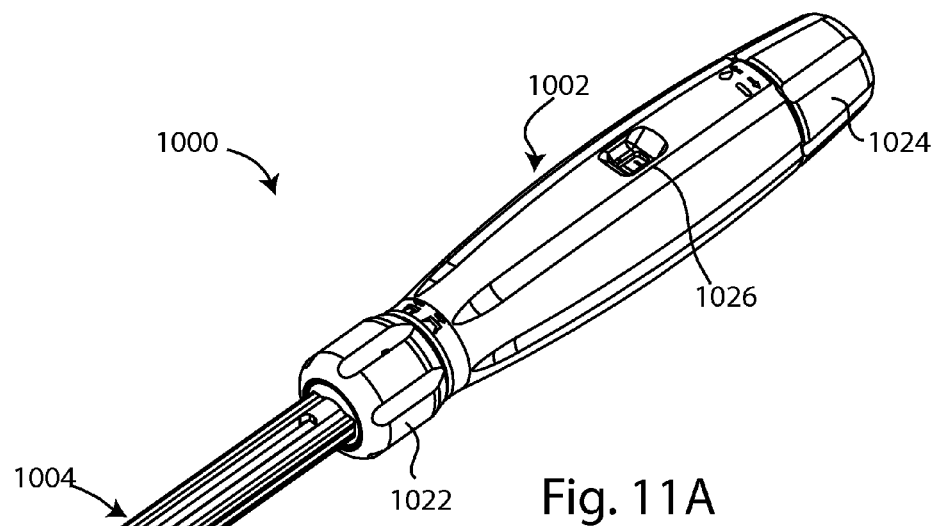
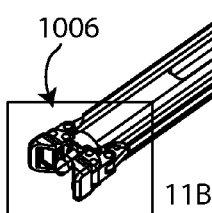
Fig. 11A
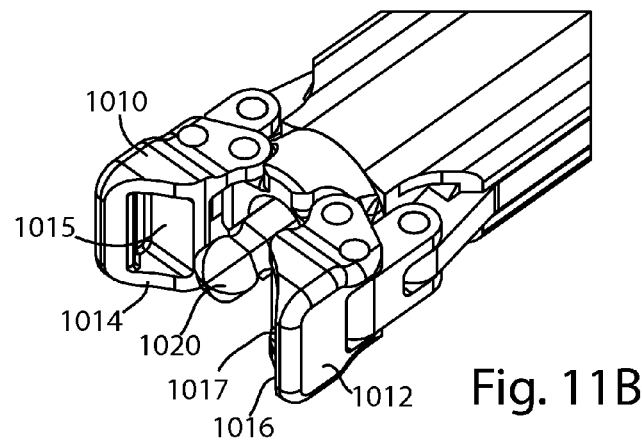
Fig. 11B

US 8,628,576 B2

EXPANDABLE INTERVERTEBRAL IMPLANTS AND INSTRUMENTS

CROSS-REFERENCE TO RELATED APPLICATIONS

This application is a non-provisional of:

pending U.S. Provisional Patent Application No. 61/442,482, filed Feb. 14, 2011, which carries, and is entitled EXPANDABLE INTERVERTEBRAL SPACER WITH SCISSOR JACK MECHANISM; and pending U.S. Provisional Patent Application No. 61/554,374, filed Nov. 1, 2011, which carries, and is entitled EXPANDING FUSION CAGE.

The above-identified documents are incorporated herein by reference.

FIELD OF THE DISCLOSURE

The present disclosure relates to spinal fusion surgery. More precisely, the present disclosure relates to a system for stabilizing two adjacent vertebral bodies to be fused.

BACKGROUND OF THE INVENTION

Intervertebral fusion may be performed to treat degenerative disc disease, spinal disc herniation, discogenic pain, spinal tumor, vertebral fracture, scoliosis, lordosis, kyphosis, spondylolisthesis, spondylosis, other degenerative spinal conditions, or any condition that causes instability of the spine. In some fusion procedures, an intervertebral implant such as a spacer or cage is placed between the vertebral bodies to provide stability. Bone graft material may be placed in the implant to promote fusion of the adjacent vertebrae.

Access to the intervertebral space between two vertebral bodies may be obtained through posterior, anterior or lateral surgical approaches. A true lateral approach requires passing through the psoas muscle to reach the intervertebral disc space. In order to minimize trauma to the muscle and the nerves in its vicinity, it may be preferable to shift the lateral trajectory anteriorly to access the anterior third of the disc space. Need exists for an implant which may be inserted from a lateral approach into the anterior portion of the disc space and expanded asymmetrically to fill the disc space.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 10A is a perspective view of an inserter instrument, with jaws of the instrument in an open configuration; and FIG. 10B is an enlarged detail view of a portion of the instrument of FIG. 10A;

FIG. 11A is a perspective view of an inserter instrument of FIG. 10A with the jaws in a closed configuration; and FIG. 11B is an enlarged detail view of a portion of the instrument of FIG. 11A;

DETAILED DESCRIPTION OF THE PREFERRED EMBODIMENTS

Figure 1:
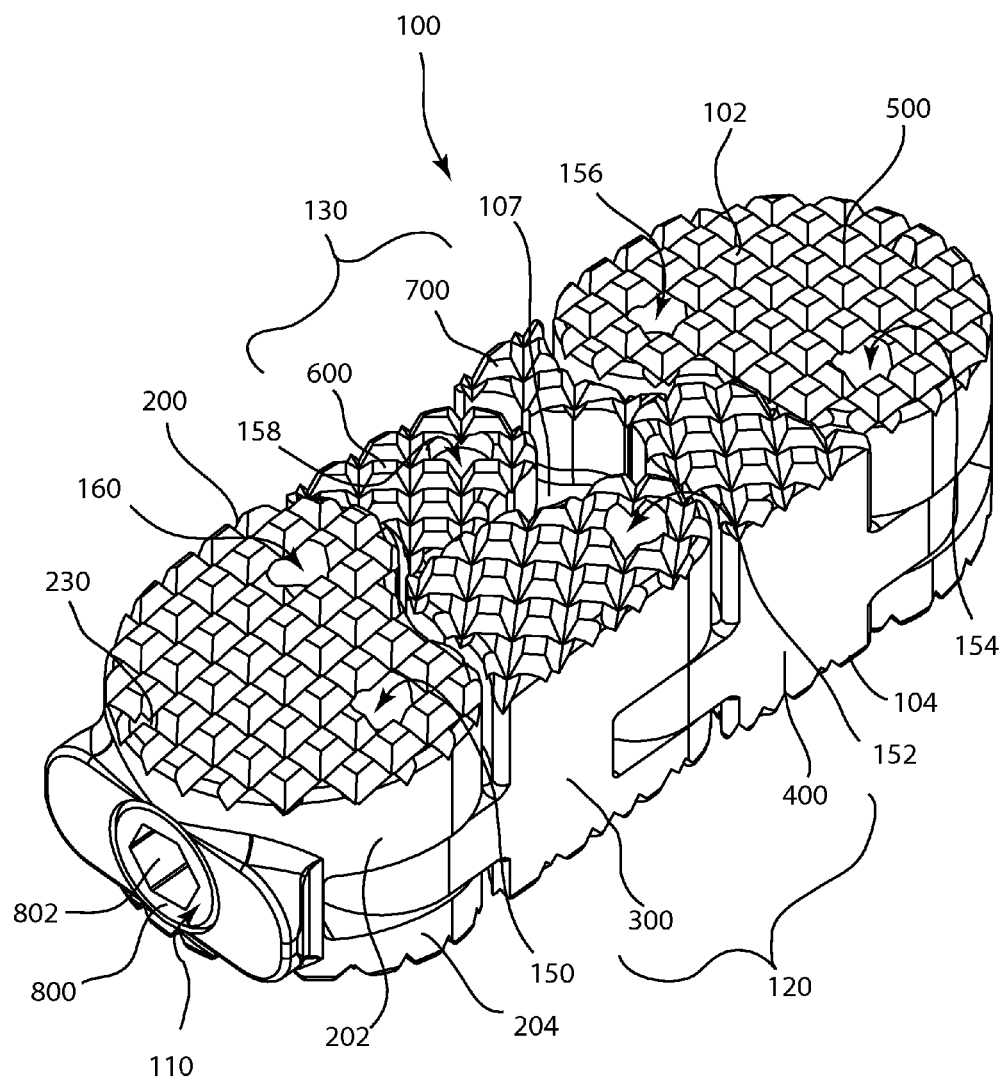
FIG. 1 is a perspective view of an expanding intervertebral fusion device in a compact configuration.
Figure 2:
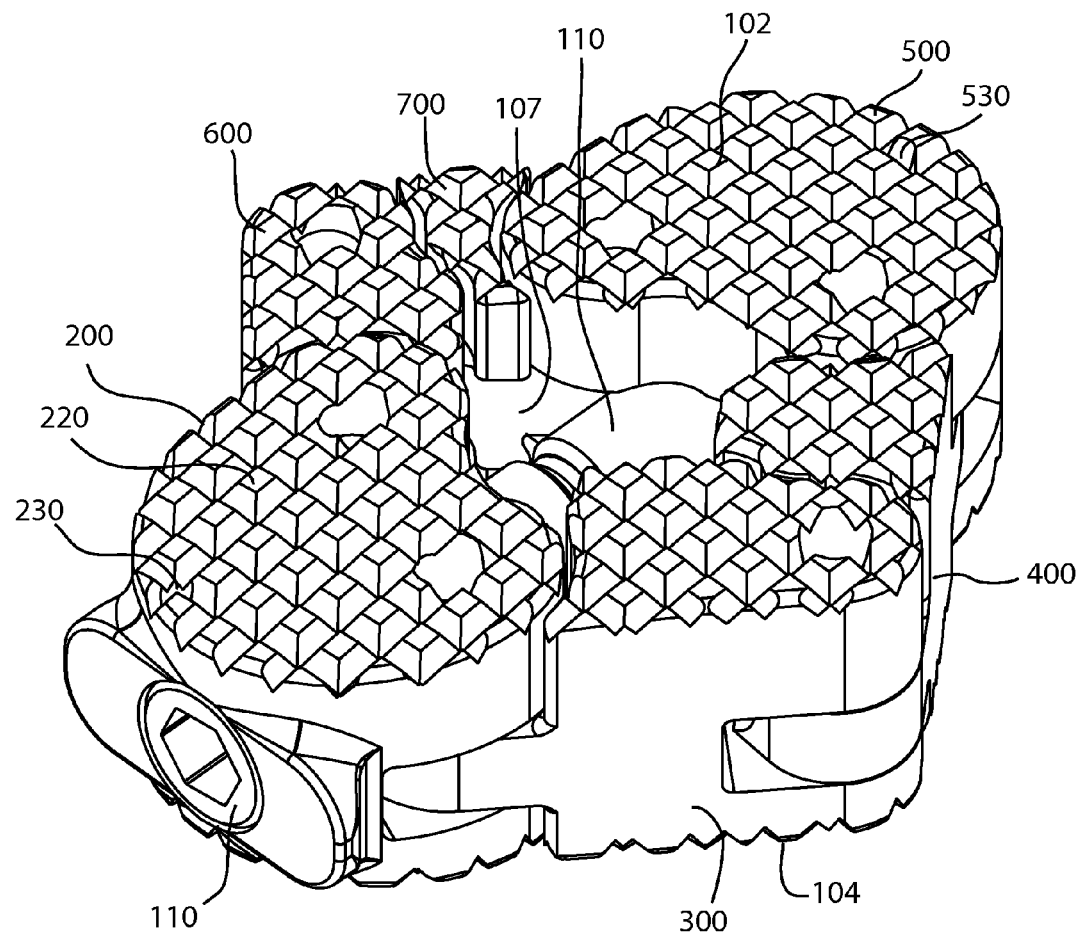
FIG. 2 is a perspective view of the fusion device of FIG. 1 in an expanded configuration.

The present disclosure provides systems, apparatus, and methods for fusion of adjacent bone portions, such as adjacent vertebral bodies in the spine. Those of skill in the art will recognize that the following description is merely illustrative of the principles of the disclosure, which may be applied in various ways to provide many different alternative embodiments. This description is made for the purpose of illustrating the general principles of this invention and is not meant to limit the inventive concepts in the appended claims. While the present disclosure is made in the context of intervertebral interbody fusion for the purposes of illustrating the concepts of the design, it is contemplated that the present design and/or variations thereof may be suited to applications outside the field intervertebral fusion. For example, the present design and/or variations thereof may be suited to applications for posterolateral fusion, or fusion of other joints.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk.

In this specification, standard spinal anatomical terms are used with their ordinary meanings.

In this specification, a standard system of three mutually perpendicular reference planes is employed. A sagittal plane divides a body into bilaterally symmetric right and left portions. A coronal plane divides a body into anterior and posterior portions. A transverse plane divides a body into superior and inferior portions.

According to a first aspect of the disclosure, an implant for implantation between a first vertebral body and a second vertebral body includes a first end body and a second end body; a first intermediate body and a second intermediate body, a portion of the intermediate bodies intermediate the first and second end bodies, the intermediate bodies movably joined to the first and second end bodies; a shaft coupled to and extending between the first end body and the second end body, the implant having an implant length parallel to the shaft and an implant width perpendicular to the shaft; wherein the implant is transformable between a compact configuration and an expanded configuration; wherein in the compact configuration the end bodies are spaced apart from one another; wherein in the expanded configuration the end bodies are closer to one another than in the compact configuration, the implant length is shortened relative to the compact configuration, and the implant width is increased relative to the compact configuration; wherein the increase in implant width is greater along a first direction of the implant width than along a second direction of the implant width.

Embodiments of this aspect of the disclosure may include one or more of the following features. The first direction is opposite the second direction. The first and second end bodies are irregularly shaped, and the first end body is shaped as a mirror image of the second end body. The first intermediate body moves at least partially along the first direction of the implant width from the shaft, wherein the second intermediate body moves at least partially along the second direction of the implant width from the shaft, and wherein the first intermediate body has a bone-contacting surface area greater than a bone-contacting surface area of the second intermediate body. The implant further including an implant window between the first and second intermediate bodies, wherein the size of the implant window is increased in the expanded configuration. The shaft increases and decreases in length to transform the implant between the compact configuration and the expanded configuration, wherein the implant length is equal to the shaft length in both the compact and expanded configurations. The shaft includes a screw, wherein turning the screw increases and decreases the length of the shaft. The first intermediate body includes a first arm movably joined to a second arm at an first interface, the second intermediate body includes a third arm movably joined to a fourth arm at a second interface, wherein the first and second interfaces limit the transformation of the implant into the expanded configuration and prevent over-expansion of the implant. The implant further including a spring, wherein the spring provides spring bias to urge the implant toward the expanded configuration. The implant further including a first bone-contacting side and a second bone-contacting side generally opposite the first bone-contacting side, an implant height measurable between the first bone-contacting side and the second bone-contacting side, the implant height perpendicular to the second bone-contacting side, wherein the implant height measured along the first direction of the implant width is greater than the implant height measured along the second direction of the implant width. Each of the first and second bone-contacting side including a plurality of bone-engagement features which project from each respective bone-contacting side. The implant is implantable with a tool, the tool including a tool shaft having a width, and wherein the width of the implant in the compact configuration is about equal to the width of the tool shaft; wherein the implant includes a shoulder and the tool includes a clamp having opposing jaws, wherein the jaws are engageable with the shoulder to grasp the implant; and wherein the tool includes a driving feature coaxially engageable with the implant shaft, wherein the tool is actuable to transform the implant between the compact and the expanded configurations. Each intermediate body is pivotably joined to each end body at a joint, wherein each joint includes a pin and at least one pin hole. The implant including a transverse plane, wherein each of the intermediate bodies is movably joined at a joint, wherein the joint includes joint housing and auxiliary housing, wherein the auxiliary housing strengthens the joint housing and stabilizes the implant across the transverse plane of the implant. The implant including an elongated gap between each end body and each intermediate body, wherein at least a section of the elongated gap maintains substantially the same width when the implant is in the compact configuration and when the implant is in the expanded configuration.

According to a second aspect of the disclosure, a method of implanting an implant between first and second vertebral bodies includes the steps of inserting an implant in between the first and second vertebral bodies, the implant including: a first end body and a second end body; a first intermediate body and a second intermediate body, a portion of the intermediate bodies intermediate the first and second end bodies, the intermediate bodies movably joined to the first and second end bodies; a shaft coupled to and extending between the first end body and the second end body, the implant having an implant length parallel to the shaft and an implant width perpendicular to the shaft; and transforming the implant between a compact configuration and an expanded configuration; wherein in the compact configuration the end bodies are spaced apart from one another; wherein in the expanded configuration the end bodies are closer to one another than in the compact configuration, the implant length is shortened relative to the compact configuration, and the implant width is increased relative to the compact configuration; wherein the increase in implant width is greater along a first direction of the implant width than along a second direction of the implant width.

Embodiments of this aspect of the disclosure may include one or more of the following features. Inserting the implant between the first and second vertebral bodies further includes inserting the implant along a lateral surgical approach. Inserting the implant between the first and second vertebral bodies further includes inserting the implant into the anterior third of an intervertebral disc space between the first and second vertebral bodies. The first direction of the implant width is a posterior direction and the second direction of the implant width is an anterior direction, wherein transforming the implant into the expanded configuration includes increasing the implant width greater along the posterior direction than along the anterior direction. The method further including mounting the implant on an tool; and actuating the tool to transform the implant from the compact configuration to the expanded configuration while the implant is between the first and second vertebral bodies.

Referring to FIGS. 1-9B, an expanding fusion device 100 is shown. The fusion device 100 may be an interbody fusion cage for insertion into an intervertebral disc space between adjacent vertebrae. The device 100, or implant, is constructed of multiple bodies connected together with hinge type joints formed by a plurality of pins 186, 188, 190, 192, 194, and 196, to form a linkage. The length of the implant 100 is defined by a shaft 110 which is coupled to two end bodies. The width of the implant 100 is perpendicular to the length. The implant 100 has a first bone-contacting side 102, a second bone-contacting side 104, a first edge 106 and a second edge 108. First and second edges 106, 108 may be perpendicular to the first and/or second bone-contacting sides 102, 104, or to a transverse plane dividing the implant into superior and inferior portions. An implant window 107 may be formed near the center of the implant 100.

Figure 4:
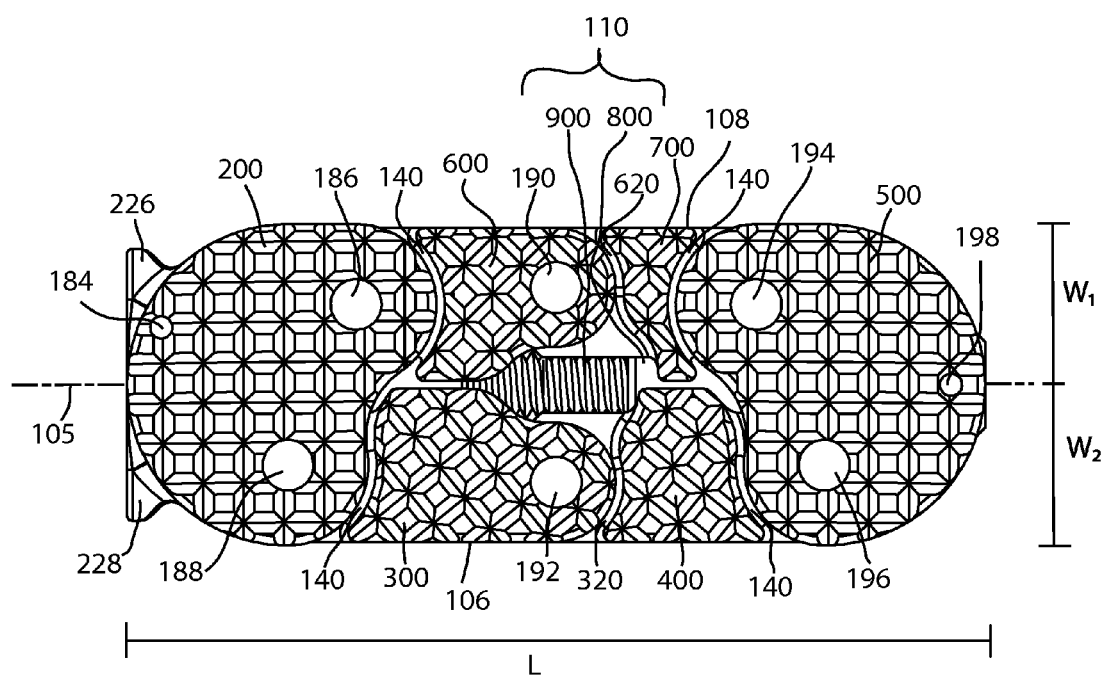
FIG. 4 is a top view of the fusion device of FIG. 1.

The implant 100 may be inserted into a disc space between two adjacent vertebrae in an initial, or compact configuration, shown in at least FIGS. 1 and 4. After insertion, the implant 100 may be reconfigured, or transformed, to a second, or expanded configuration, shown in at least FIGS. 2 and 5, that increases the width of the implant, and may increase the contact ring with the associated bone. For example, the associated bone may be vertebral endplates defining an intervertebral disc space. The implant 100 may be inserted using a lateral approach to the lumbar spine. For example, with reference to FIGS. 4 and 5, the implant 100 may be positioned in the intervertebral disc space with the pin 190 anterior, the pin 192 posterior, the pin 198 to the left, and the pin 184 to the right. In this arrangement, the expansion of the implant 100 extends the contact between the implant and the vertebral endplates in both the anterior and posterior directions, resulting in greater construct stability. In this arrangement, the first bone-contacting side 102 may be an upper, or superior side of the implant and the second bone-contacting side 104 may be a lower, or inferior side. In this arrangement, first edge 106 may be a posterior edge and second edge 108 may be an anterior edge.

Referring to FIGS. 1-4, implant 100 includes a first end body 200 and a second end body 500, each end body coupled to a portion of the shaft 110. Each end body may be irregularly shaped, and the shape of the one end body may be a mirror image of the shape of the other end body. In the embodiment shown, the end bodies 200, 500 have irregular kidney shapes, but other irregular and regular shapes are contemplated. First end body 200 includes an upper or first end body section 202 joined to a lower or second end body section 204. An end body gap 206 is between the first and second end body sections 202, 204. Two joint pin holes 208, 210 each extend through the first and second end body sections 202, 204. The upper exterior surface of the first end body 200 is a first bone engagement surface 214, which may be superiorly oriented. The lower exterior surface of the second end body section 204 is a second bone engagement surface 216, which may be inferiorly oriented. One or more bone engagement features such as teeth 220 may project from the bone engagement surfaces 214, 216. In other embodiments, bone engagement features may include teeth, spikes, pins, posts, points, surface roughening, bosses, ridges, or keels, among others. The size and/or distribution of the bone engagement features may vary.

First end body section 202 is circumscribed by a first end body section periphery 203, which may be smooth and include rounded curves. Similarly, second end body section 204 is circumscribed by a second end body section periphery 205, which may be smooth and include rounded curves. The smooth surface and rounded curves may promote smooth articulation with intermediate bodies of the implant.

First end body 200 includes a shaft retainer 222, which may include opposed grooves formed into first and second end body sections 202, 204, opening into end body gap 206. Shaft retainer 222 includes a shaft opening 224 flanked by shoulders 226, 228. A shaft pin hole 230 extends through the first end body section and opens into the shaft opening 224. A shaft retention pin 184 is shaped to be received in shaft pin hole 230 to retain a portion of shaft 110 in the shaft retainer 222 so that the shaft is rotatable about its center longitudinal axis, and otherwise fixed to the first end body 200.

Second end body 500 includes an upper or first end body section 502 joined to a lower or second end body section 504. An end body gap 506 is between the first and second end body sections 502, 504. Two joint pin holes 508, 510 each extend through the first and second end body sections 502, 504. The upper exterior surface of the second end body 500 is a first bone engagement surface 514, which may be superiorly oriented. The lower exterior surface of the second end body section 504 is a second bone engagement surface 516, which may be inferiorly oriented. One or more bone engagement features such as teeth 220 may project from the bone engagement surfaces 514, 516. In other embodiments, bone engagement features may include teeth, spikes, pins, posts, points, ridges, grooves, surface roughening, bosses, or keels, among others. The size and/or distribution of the bone engagement features may vary.

First end body section 502 is circumscribed by a first end body section periphery 503, which may be smooth and include rounded curves. Similarly, second end body section 504 is circumscribed by a second end body section periphery 505, which may be smooth and include rounded curves. The smooth surface and rounded curves may promote smooth articulation with intermediate bodies of the implant.

Second end body 500 includes a shaft retainer 522, which may include opposed grooves formed into first and second end body sections 502, 504, opening into end body gap 506. A shaft pin hole 530 extends through the first and second end body sections 502, 504 and. A shaft retention pin 198 is shaped to be received in shaft pin hole 530 to retain a portion of shaft 110 in the shaft retainer 522 so that the shaft is fixed to the second end body 500.

The implant 100 may be moved or transformed between the closed and expanded configurations by means of a two-piece adjustment mechanism. Shaft 110 includes a male half 800 and a female half 900. The male half 800 includes a socket 802. In the illustrated example, the male half 800, or screw, is placed through the first end body 200, into the shaft retainer 222 and is held captive to the end body 200 by a shoulder-to-shoulder thrust surface contact and pin 184 in shaft pin hole 230 to retain the screw 800 in the implant 100. The female half 900, or socket, is placed through the second end body 500 into shaft retainer 522 and is retained in place by means of a cross pin 198. A portion of screw 800 is threadably received in socket 900. In this arrangement, turning the screw 800 relative to the socket 900 causes the end bodies 200, 500 to move closer together or farther apart. The screw 800 and socket 900, forming shaft 110, may be said to establish a central longitudinal axis 105 of the device 100. The engagement length between the two screw halves 800, 900 may be maximized because the mechanism has a secondary function of maintaining proper alignment between the first and second end bodies 200, 500 along the central longitudinal axis of the implant 100. In alternate embodiments, shaft 110 may be a jackscrew, telescoping member, turnbuckle, ratchet, or other variable length coupling.

A first intermediate body 120 and a second intermediate body 130 are each disposed at least partially between, or intermediate, the first and second end bodies 200, 500. The intermediate bodies are movably joined to the end bodies, allowing the expansion in the width of the implant. First intermediate body 120 includes two subunits, a first arm 300 and a second arm 400. First arm 300 is movably connected to first end body 200 at a joint 150, and to second arm 400 at a joint 152. Second arm 400 is movably connected to second end body 500 at joint 154. First arm 300 includes a tab 302 and a slot 304. Two pin holes 306, 308 extend through tab 302 and slot 304, respectively. Bone-contacting surfaces 310, 312 are formed on opposing sides of the first arm 300. Second arm 400 includes two tabs 402, 404 with pin holes 406, 408. Bone-contacting surfaces 410, 412 are formed on opposing sides of the second arm 400.

Second intermediate body 130 includes two subunits, a third arm 600 and a fourth arm 700. Third arm 600 is movably joined to first end body 200 and fourth arm 700 at joints 160, 158, and fourth arm 700 is movably joined to second end body 500 and third arm 600 at joints 156, 158. Third arm 600 includes a tab 602 and a slot 604. Two pin holes 606, 608 extend through tab 602 and slot 604, respectively. Bone-contacting surfaces 610, 612 are formed on opposing sides of the third arm 600. Fourth arm 700 includes two tabs 702, 704 with pin holes 706, 708. Bone-contacting surfaces 710, 712 are formed on opposing sides of the fourth arm 700. Any of the bone-contacting surfaces may include one or more bone engagement features as described previously. In other embodiments bodies 200, 500 and arms 300, 400, 600, 700 may be bodies, arms, beams, links, wall elements, units, subunits, spacers, or plates, among other suitable members.

Figure 3:
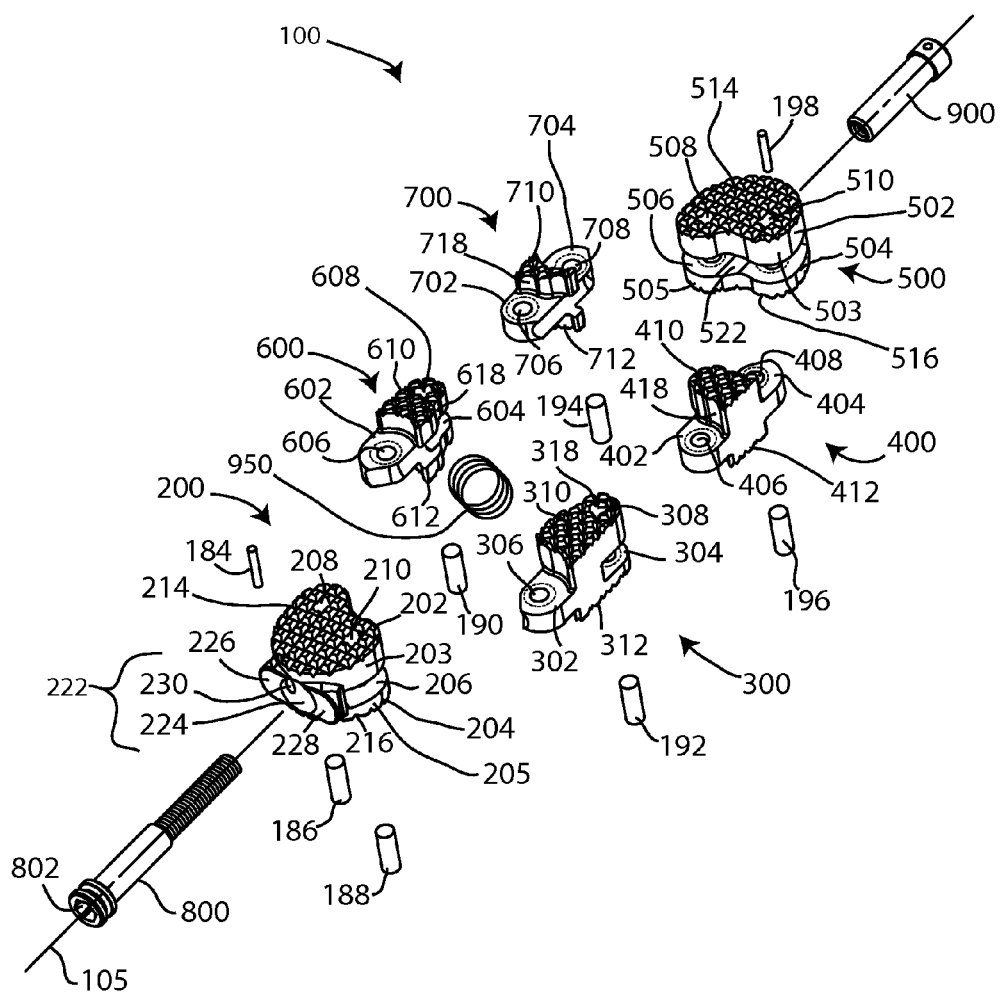
FIG. 3 is an exploded perspective view of the fusion device of FIG. 1.

The joints between the end bodies and arms, and between the arms, may be hinge type connections. Each joint 150, 152, 154, 156, 158, 160 may include a pin extending through at least two pin holes. Implant material immediately surrounding each pin hole may be referred to as joint housing. Referring to FIG. 3, the joint housing around selected pin holes is indicated by the area within the dashed line encircling the pin holes, and represents the minimum material needed to support the joint and permit it to function, allowing pivoting of the respective end bodies or arms about the pin. Material outside the dashed lines may be referred to as auxiliary housing, and represents material in excess of the minimum needed, the auxiliary housing functioning to reinforce and strengthen the joint housing, and stabilize the implant across the transverse plane of the implant. The additional structure provided by the auxiliary housing may prevent flexing of the implant 100 across the transverse plane of the implant. Each of the joints of implant 100 includes joint housing and auxiliary housing.

Arms 300, 400, 600 and 700 are each irregularly shaped. The total bone-contacting surface area of first intermediate body 120, which includes bone-contacting surfaces 310, 410 on one side and bone-contacting surfaces 312, 412 on the opposing side, is greater than the total bone contacting surface area of the second intermediate body 130. Where each end body 200, 500 interfaces with each intermediate body 120, 130, there is an elongated gap 140, or clearance between the periphery of the end body and the adjacent intermediate body. As may be seen in FIGS. 4 and 5, whether implant 100 is expanded or compact, the width of the elongated gap between the opposing peripheral surfaces of the end bodies and the intermediate bodies remains substantially constant. This is in contrast to, for example, a door or piano type hinge in which the gap between the opposing surfaces widens as the door is opened, forming a V shape.

Pins 186, 188, 190, 192, 194, and 196 each form a pivot point, or pivot axis about which the end bodies and intermediate bodies pivot to transform the implant 100 between the compact and expanded configurations. Pin 188 extends through pin holes 210 and 306 to pivotably connect, or hinge end body 200 to first arm 300 at joint 150. Pin 192 extends through pin holes 308 and 406 to pivotably connect, or hinge first arm 300 to second arm 400 at joint 152. Pin 196 extends through pin holes 510 and 408 to pivotably connect, or hinge second arm 400 to second end body 500 at joint 154. Pin 194 extends through pin holes 508 and 708 to pivotably connect, or hinge second end body 500 to fourth arm 700 at joint 156. Pin 194 extends through pin holes 608 and 706 to pivotably connect, or hinge fourth arm 700 to third arm 600 at joint 158. Pin 186 extends through pin holes 208 and 606 to pivotably connect, or hinge third arm 600 to end body 200 at joint 160. These pivotable joints allow the expansion and contraction of the implant 100. The pivoting movement of the arms during expansion or contraction may be referred to as scissor-jack movement. It is appreciated that in other embodiments, more arms or subunits could be included with suitable pivotable connections or joints. One example includes a lattice type construction with multiple arms interconnected with pivotable connections. It is also appreciated that in other embodiments, the end bodies may be pivotably connected to each other.

Figure 5:
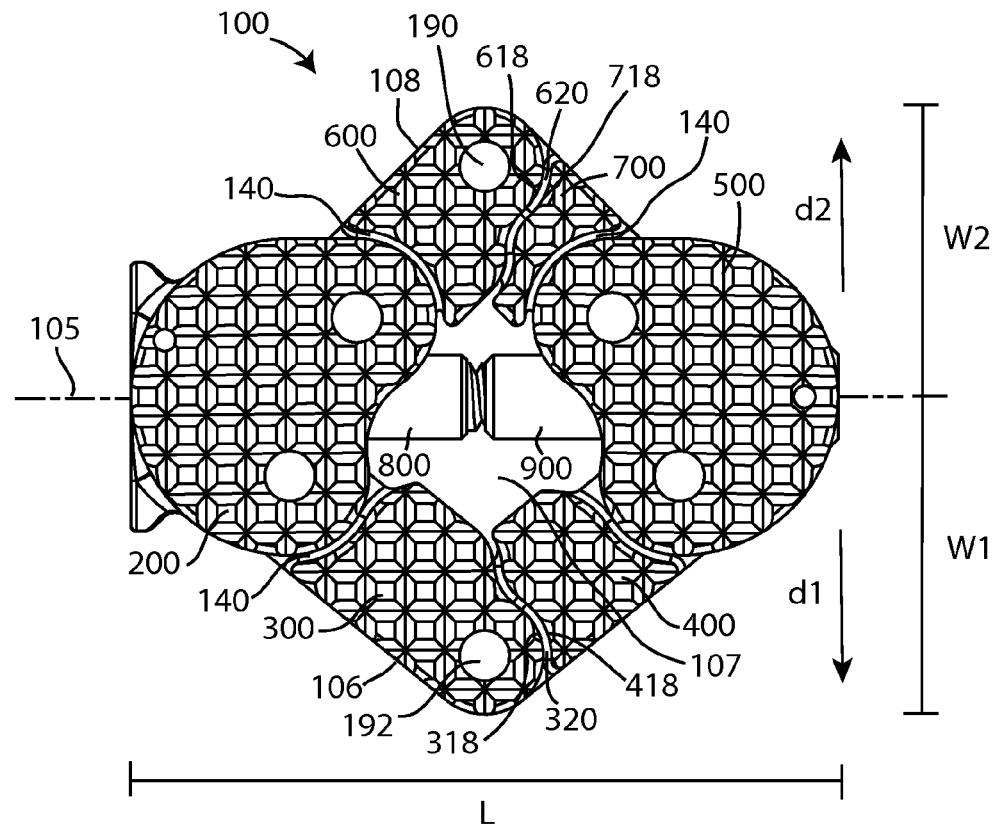
FIG. 5 is a top view of the fusion device of FIG. 2.

Referring to FIGS. 3-5, arm 300 interfaces with arm 400 at a first interface 320, and arm 600 interfaces with arm 700 at a second interface 620. The interfaces 320, 620 limit the transformation of the implant into the expanded configuration and prevent over-expansion of the implant. Arm 400 includes an articulation surface 418, arm 300 includes an articulation surface 318, arm 600 includes an articulation 618, and arm 700 includes an articulation surface 718. The articulation surfaces may include curves, and may be complexly curved. Articulation surfaces 418, 718 may provide stops to expansion of implant 100 beyond a selected limit. For example, as seen in FIG. 5 once the articulation surface 718 of arm 700 fully encounters an opposing articulation surface 618 of arm 600, the interface 620 limits any further movement of 600 and 700 relative to one another in that direction. Similarly, articulation surfaces 318, 418 may cooperate in the expanded configuration to prevent further expansion of the implant.

Referring to FIGS. 4 and 5, implant 100 has an implant length L and an implant width W. The implant length may be defined by the length of the shaft 110 along a longitudinal axis 112, and may vary between the compact configuration and the expanded configuration. In the examples shown, length L is longest in the compact configuration and shortest in the expanded configuration. The implant width W is measured at the widest point crossing the implant from one outer edge of the implant across one or more of the bodies 200, 300, 400, 500, 600, 700, to an opposite outer edge of the implant, measured perpendicular to the longitudinal axis 112 of the shaft 110. In the examples shown, width W is narrowest in the compact configuration and widest in the expanded configuration. The width W may have a first segment $W_1$ measured in a first direction d1 perpendicular to the implant length, and a second segment $W_2$ measured in a second direction d2 perpendicular to the implant length and opposite the first direction, wherein $W=W_1+W_2$. As implant 100 is transformed from the compact configuration to the expanded configuration, the increase in the first width segment, along the first direction, may be greater than the increase in the second width segment, along the second direction. This may be called asymmetric expansion. Asymmetric expansion may be advantageous when using a lateral surgical approach. A true lateral approach requires passing through the psoas muscle to reach the intervertebral disc space. In order to minimize trauma to the muscle and the nerves in its vicinity, it may be preferable to shift the lateral trajectory anteriorly to access the anterior third of the disc space. An implant that expands more in the posterior direction than in the anterior direction may more effectively fill the disc space, resulting in a more stable final construct. In the example shown and described, the first direction d1 may be posterior and the second direction may be anterior d2.

Figure 6A:
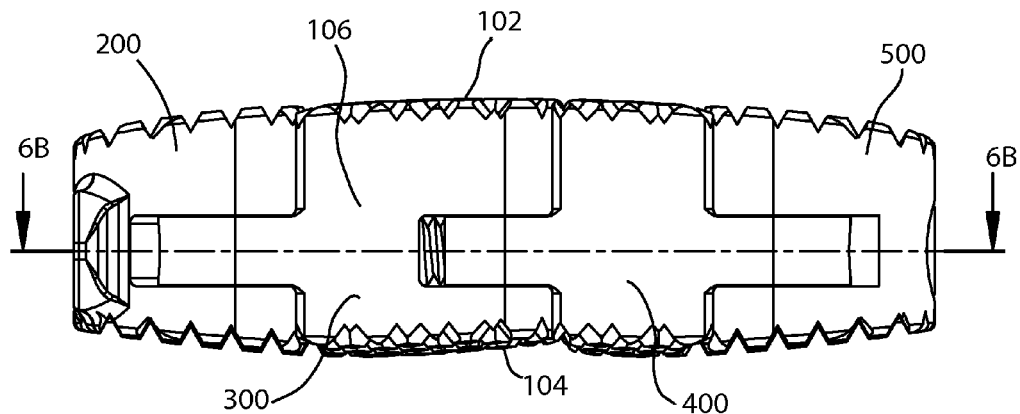
FIG. 6A is a side view of the fusion device of FIG. 1.
Figure 6B:
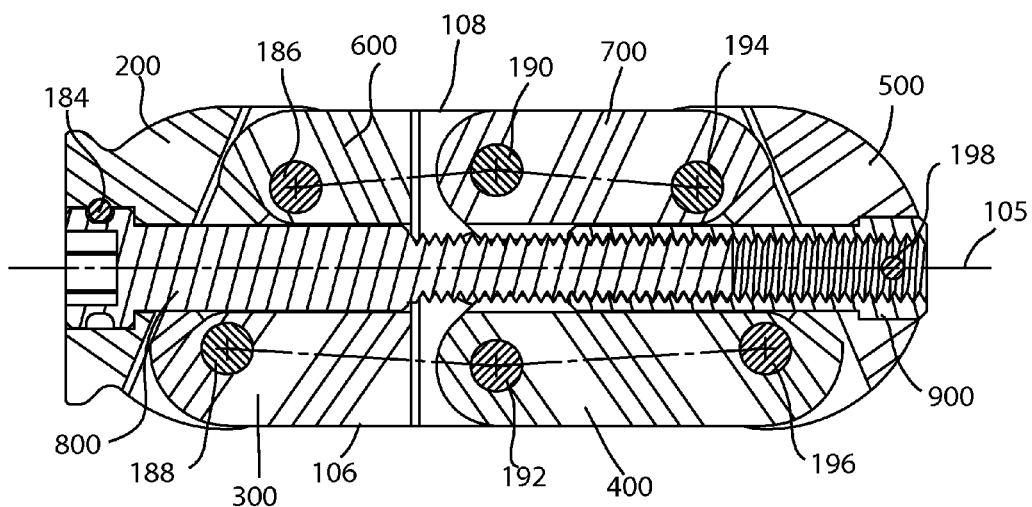
FIG. 6B is a cross section view of the fusion device of FIG. 1 taken along section line 6B-6B shown in FIG. 6A.
Figure 7A:
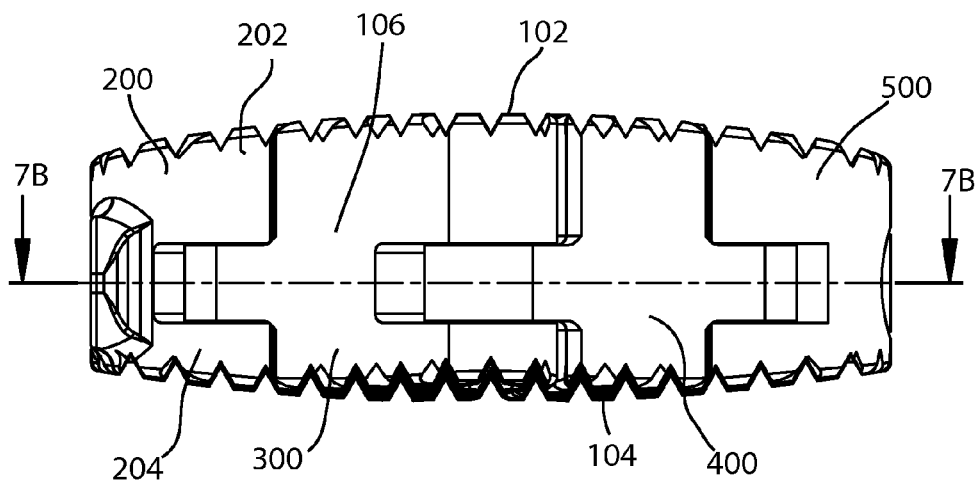
FIG. 7A is a side view of the fusion device of FIG. 2.
Figure 7B:
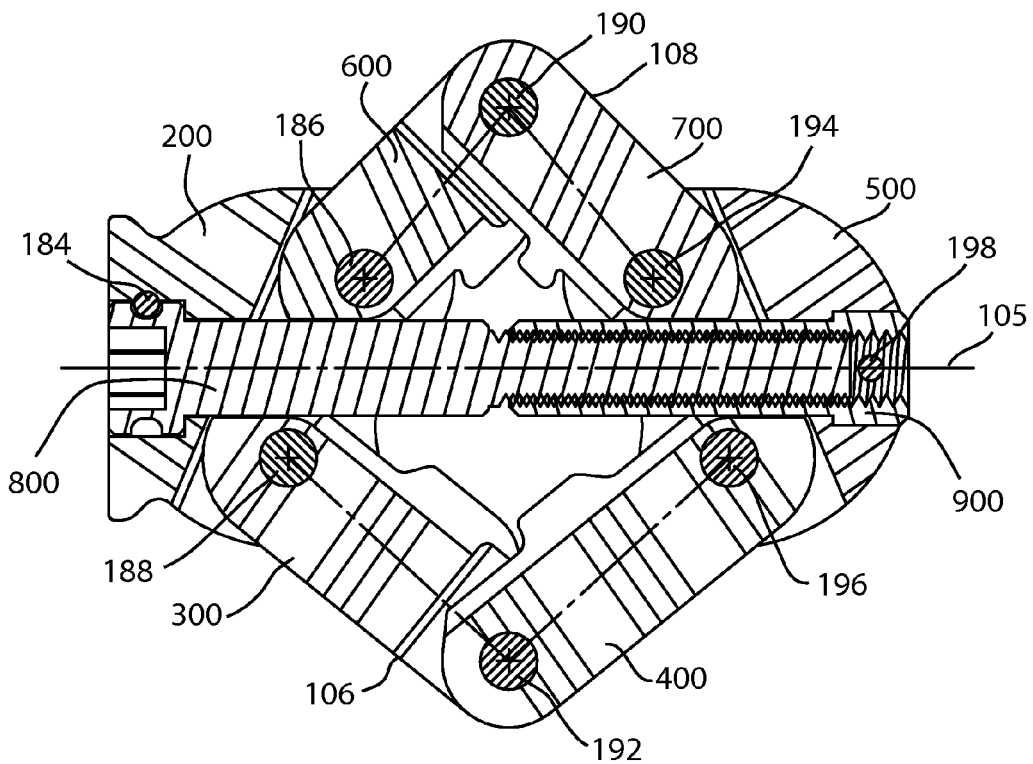
FIG. 7B is a cross section view of the fusion device of FIG. 2 taken along section line 7B-7B shown in FIG. 7A.

FIGS. 6A-7B further illustrate the compact and expanded configurations of implant 100. FIG. 6A is a side view of implant 100 in the compact configuration, and FIG. 6B is a cross-sectional view taken along line B-B in FIG. 6A. FIG. 7A is a side view of implant 100 in the expanded configuration, and FIG. 7B is a cross-sectional view taken along line B-B in FIG. 7A.

The compact configuration may also be described as a closed configuration, a reduced size configuration, an initial configuration, or an insertion configuration. Referring to FIGS. 1, 4, 6A-B, and 9B, in the closed configuration, the bodies 200 and 500 are positioned so that the bodies 300, 400, 600, and 700 extend more or less straight between the bodies 200, 500. In this arrangement, the device 100 has a relatively small profile or cross sectional area perpendicular to the center longitudinal axis 105 of the device 100. It can be appreciated that pin 190 is displaced farther away from the center longitudinal axis than pins 186 and 194, and pin 192 is displaced farther away from the center longitudinal axis than pins 188 and 196, even in the closed configuration. This arrangement may facilitate transforming the implant to the expanded configuration.

The expanded configuration may also be described as a larger size configuration, a final configuration, or an implanted configuration. Referring to FIGS. 2, 5, 7B, and 8B, in the expanded configuration, the bodies 200 and 500 are positioned so that the bodies 300, 400, 600, and 700 are angled outwardly from the center longitudinal axis of the device 100. More specifically, in the expanded configuration, pins 190, 192 are displaced farther away from the center longitudinal axis 105 than their respective positions in the closed configuration. In use, the device 100 may be inserted into an intervertebral disc space so that expansion takes place in the transverse plane, or in a plane parallel to one of the vertebral endplates defining the intervertebral disc space, or in a plane parallel to the plane that is equidistant from these vertebral endplates. In this arrangement, the expanded configuration increases the effective contact area between the device 100 and the vertebral endplates. The size of the implant window 107 may also be increased in the expanded configuration.

Figure 8A:
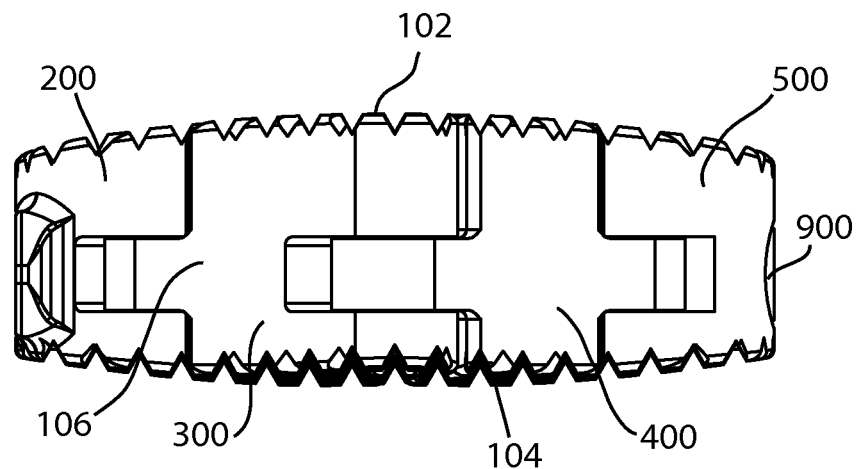
FIG. 8A is a side view of the fusion device of FIG. 2.
Figure 8B:
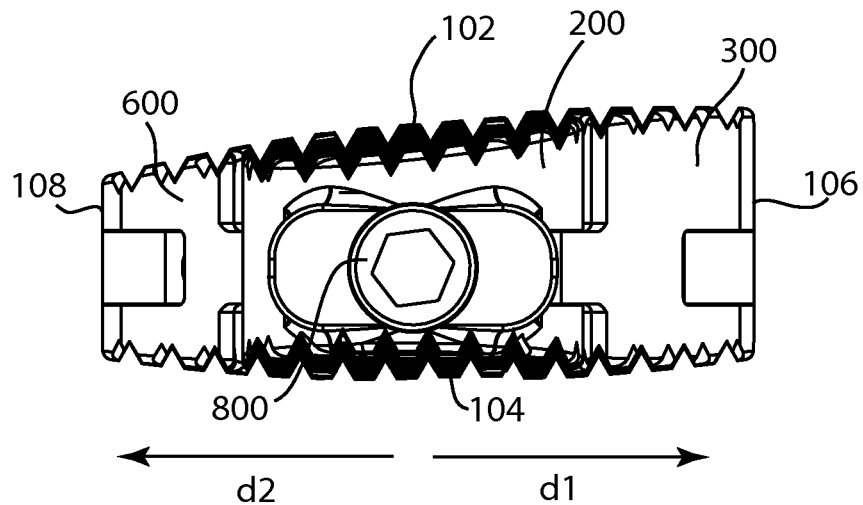
FIG. 8B is an end view of the fusion device of FIG. 2.
Figure 9A:
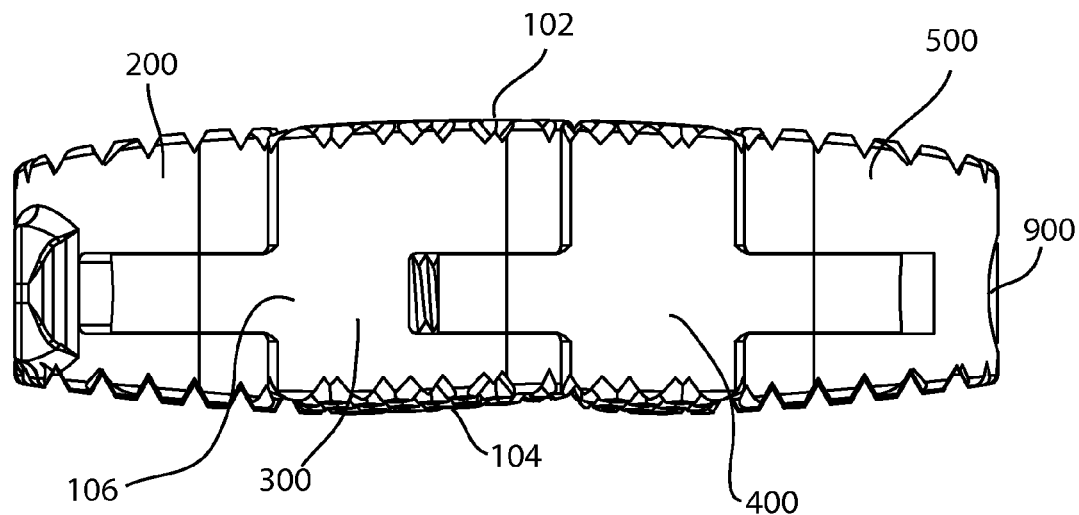
FIG. 9A is a side view of the fusion device of FIG. 1.
Figure 9B:
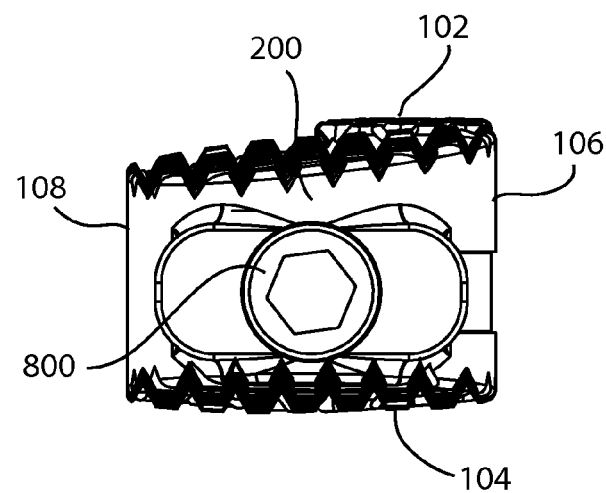
FIG. 9B is an end view of the fusion device of FIG. 1.
Figure 12A:
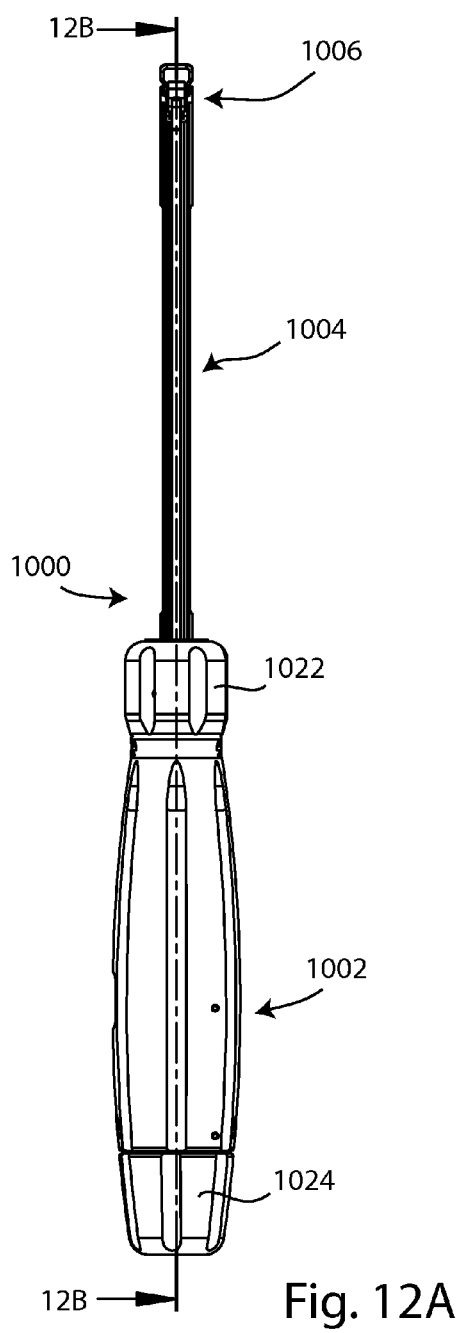
FIG. 12A is a side view of the instrument of FIG. 10A.
Figure 12B:
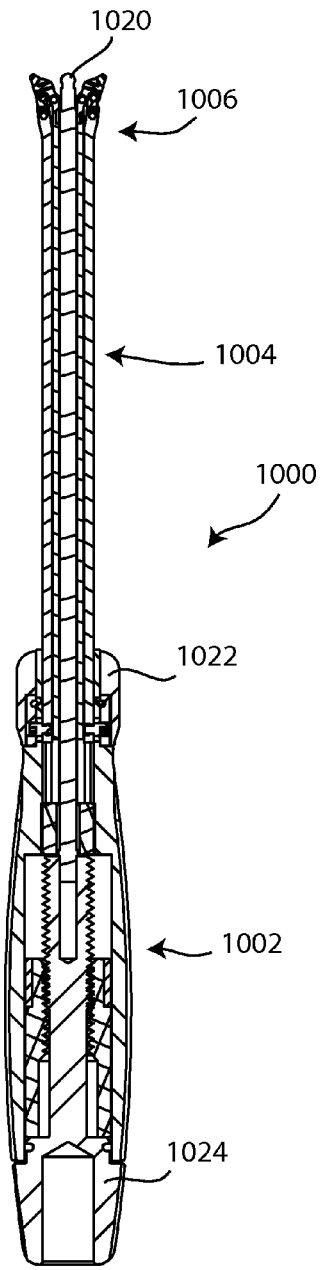
FIG. 12B is a cross section view of the instrument of FIG. 10A taken along section line 12B-12B shown in FIG. 12A.

It is frequently desirable to use an implant that includes a lordotic angle that matches the patient's natural spinal curvature. The disclosed implant 100 includes a lordotic curvature that is consistent or congruent across all the implant bodies 200, 300, 400, 500, 600, and 700 when the implant 100 is in the expanded position, as may be seen in FIGS. 8A-B. As a consequence, the bone-contacting surfaces 102, 104 may not be consistent when the implant is in the insertion or compact configuration, as shown in FIGS. 9A-B.

The height of the implant may be measured as the distance between the first and second bone-contacting surfaces 102, 104. The height maybe measured at first edge 106, second edge 108, or between the first and second edges and generally perpendicular to the second bone-contacting surface 104. As seen in FIG. 8B, the implant height measured along first direction d1, toward the first side 106 is greater than the implant height measured along the second direction d2, toward the second side 108. The asymmetric expansion of implant 100 is also visible in FIG. 8B. In the example shown, when implant 100 is inserted into the disc space between two vertebral bodies and expanded as described herein with direction d1 pointing posteriorly, the implant 100 will provide a lordotic correction, as the implant increases in height from the anteriorly oriented second edge 108 to the posteriorly oriented first edge 106. In alternative embodiments the implant may provide a kyphotic or scoliotic correction, by being implanted in a different orientation and/or by forming the implant with the height differential toward a different edge or end of the implant.

FIGS. 10A-12B show an example of an inserter instrument, or tool, for the expanding fusion device. The inserter 1000 includes a handle portion 1002, a shaft portion 1004 and a working end 1006. Working end 1006 includes a pair of opposing first and second jaws 1010, 1012 which may clamp onto the implant 100. Other styles of clamps or connections can be envisioned to achieve the same outcome. The inserter 1000 may also include a drive tip 1020 which engages the screw 800 to transmit torque to move the implant 100 between the compact and expanded configurations. The width of the shaft portion 1004 is about equal to the width of the implant 100 in the compact configuration. This allows the implant and inserter shaft to pass through a minimal sized cannula during an insertion or removal process.

Referring to FIGS. 10B and 11B, enlarged views of working end 1006 show details of the jaws 1010, 1012 and drive tip 1020. First jaw 1010 includes a clamping surface 1014 and a recess 1015, and opposing second jaw 1012 similarly includes a clamping surface 1016 and a recess 1017. The drive tip 1020 may be shaped to complementarily engage with screw socket 802. Moving and locking the jaws may be accomplished via actuation of a control mechanism on the inserter 1000. For example a first knob 1022 of the handle 1002 may be rotated to move, lock or unlock the jaws. In other embodiments a lever, button or tab may be actuated to move, lock or unlock the jaws. Another control mechanism on the inserter 1000 may be actuated to drive the drive tip 1020. For example, a second knob 1024 on the handle portion 1002 may be rotatable to rotate the tip 1020. An indicator 1026 may be present on the inserter 1000 to indicate the degree of actuation of tip 1020, so the surgeon can tell to what degree the implant has been expanded.

Figure 13:
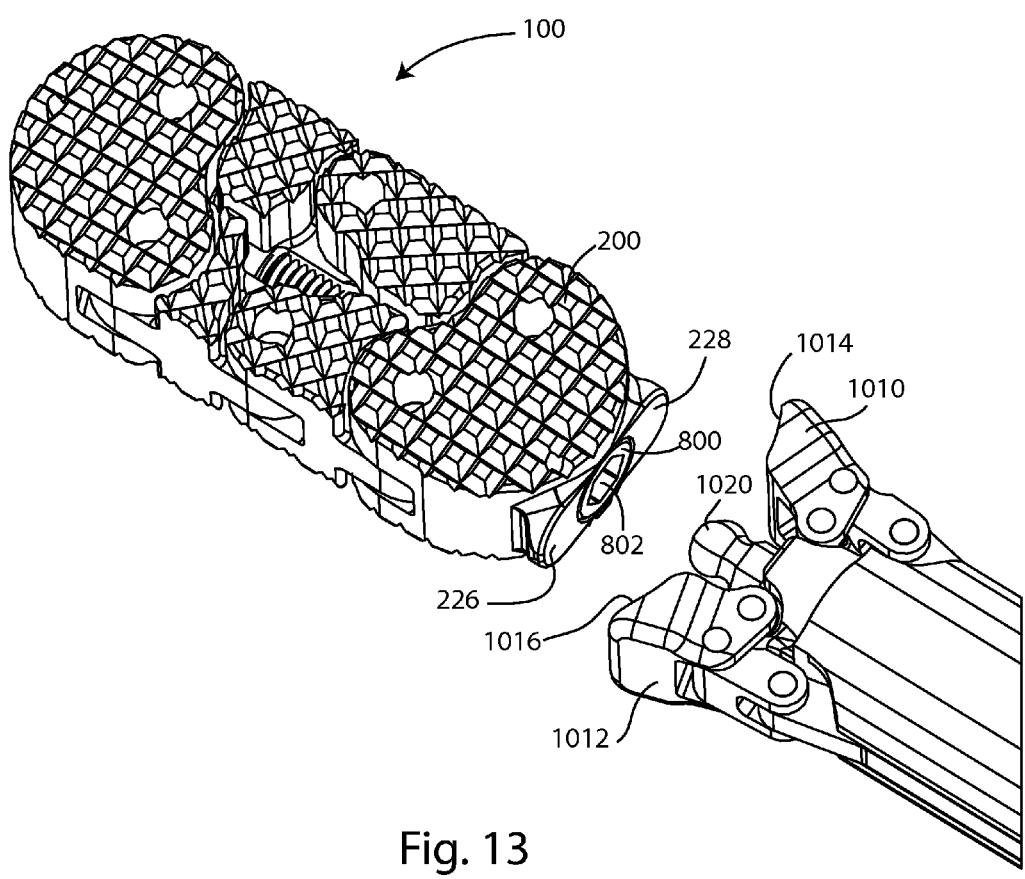
FIG. 13 is an enlarged detail view of the fusion device of FIG. 1 and a portion of the instrument of FIG. 10A.
Figure 14:
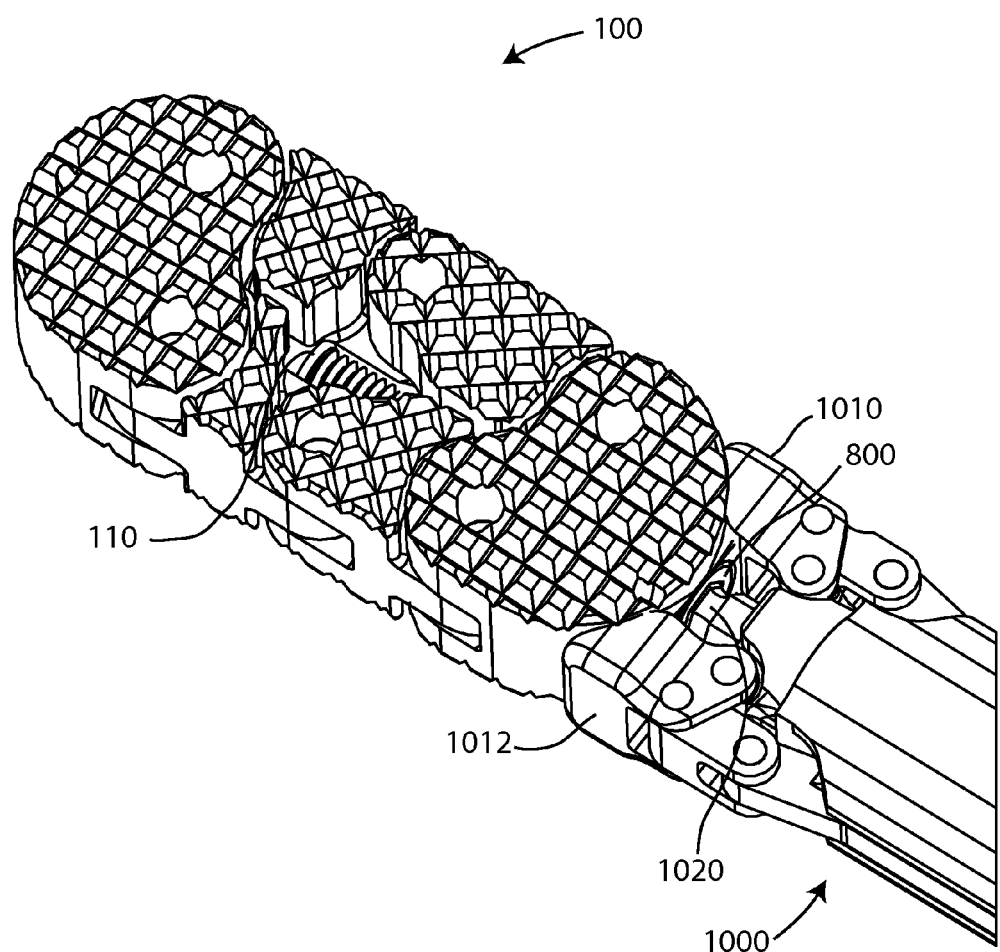
FIG. 14 is an enlarged detail view of the fusion device and instrument portion of FIG. 13 coupled together, the implant in the compact configuration.
Figure 15:
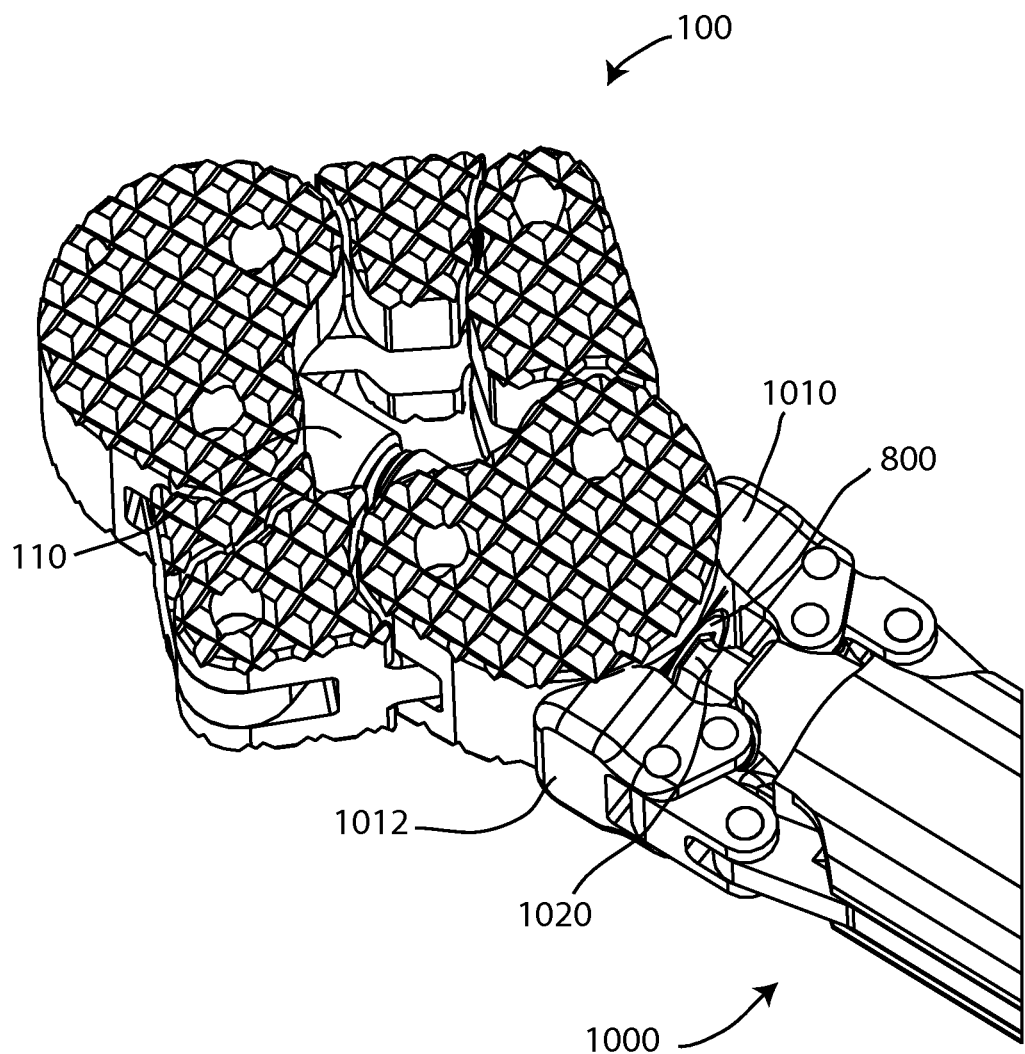
FIG. 15 is an enlarged detail view of the fusion device and instrument portion of FIG. 13 coupled together, the implant in the expanded configuration.

In use, handle portion 1002 of inserter 1000 may be actuated to open jaws 1010, 1012 into the open position seen in FIGS. 10A and 10B. Referring to FIGS. 13 and 14, the implant 100 may be mounted on the inserter 1000 with drive tip 1020 coaxially received in screw socket 802. Clamping surfaces 1014, 1016 abut end body 200 with shoulders 226, 228 received in recesses 1017, 1015. The interface between the shoulders and recesses may be a dovetail interface or other undercut interface. Once the implant 100 is mounted on the inserter, the jaws 1010, 1012 may be moved to the closed position seen in FIGS. 11A, 11B and 14, and may be locked in the closed position. In this arrangement, with implant 100 in the compact configuration and mounted on inserter 1000, the implant 100 may be inserted, or implanted, into an intervertebral space between the endplates of two adjacent vertebral bodies. The implantation may be along a lateral approach into the anterior third of the intervertebral space. After insertion of the compact implant to the intervertebral space, drive tip 1020 may be actuated, or rotated to turn screw 800. As set forth above, actuation of screw 800 may shorten shaft 110 and simultaneously expand the width of the implant, as arms 300, 400, 600, 700 are urged outward. The expansion may be asymmetrical, with the implant 100 expanding further toward the posterior direction.

Variations of the implant 100 are contemplated. For example, the implant 100 may be provided with different overall heights covering a range of intervertebral disc heights. In other examples, the implant 100 may be provided with different lordotic and/or kyphotic angles. In still other examples, the implant 100 may be provided with other patterns or features, such as spikes, keels, or the like on the bone contacting surfaces that provide stability and/or resistance to shifting positions. The implant may be made from metal, polymer, ceramic, composite, or other biocompatible and sterilizable material. Different materials may be combined in what is described herein as a single part.

The screw 800 and/or socket 900 may be fenestrated so that bone graft, marrow, or other therapeutic or structural material may be introduced into the expanded implant center, or implant window 107.

In an embodiment, one or more springs may be included in the implant to provide spring bias to urge the implant toward the expanded configuration. For example, a spring 950 may be included between the first and second intermediate bodies 120, 130 to urge the implant toward the expanded configuration. In this arrangement, the various parts of the implant may be configured so that pin 190 is even with or closer to the center longitudinal axis 105 than pins 186 and 194, and pin 192 is even with or closer to the center longitudinal axis 105 than pins 188 and 196 in the closed configuration.

Variations of the inserter 1000 are contemplated. For example, alternate complementary implant/inserter interfaces may be provided. In other examples, alternate mechanisms may be provided to actuate the implant grasping features of the inserter 1000. The implant grasping and driving features may be provided on separate instruments.

Figure 16:
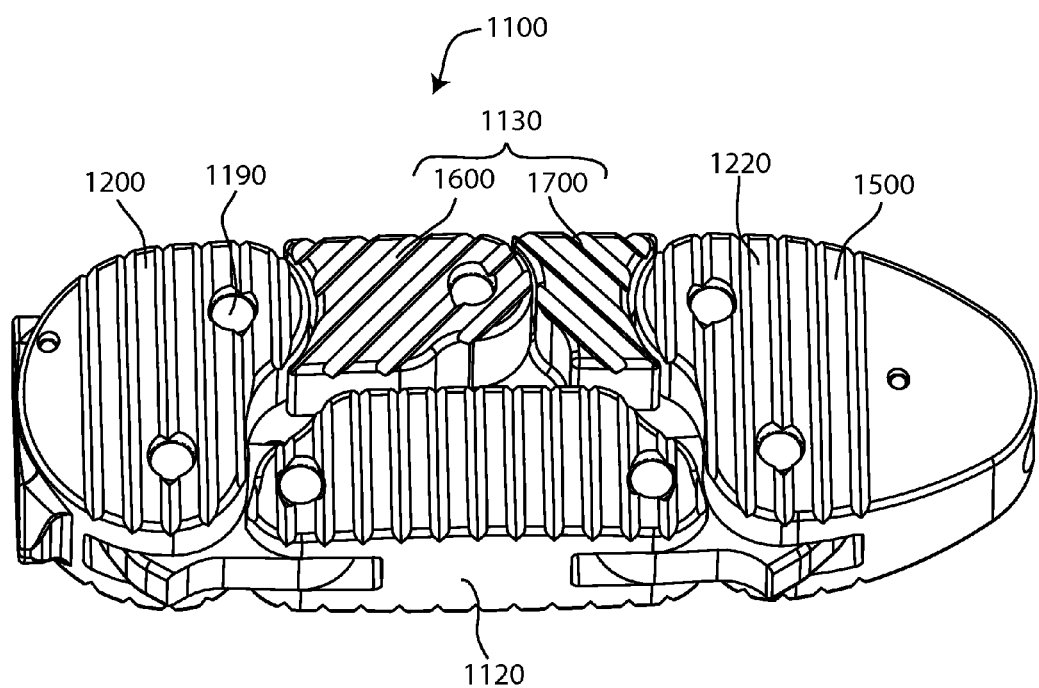
FIG. 16 is a perspective view of an alternate embodiment of an expanding fusion device, the fusion device in a compact configuration.
Figure 17:
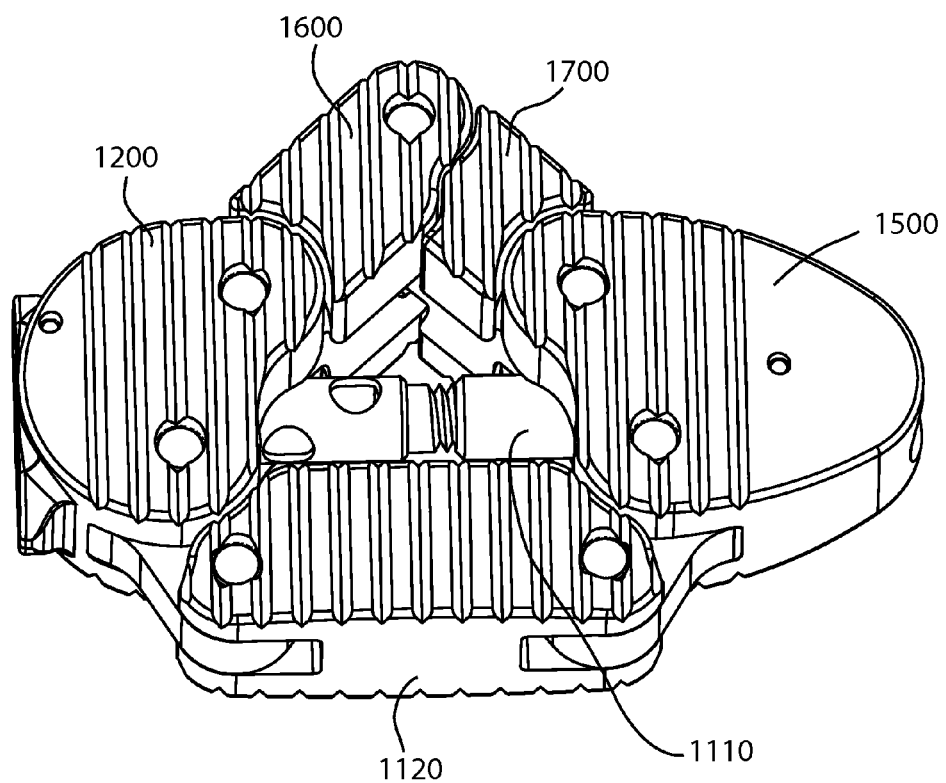
FIG. 17 is a perspective view of the fusion device of FIG. 16, the fusion device in an expanded configuration.

An alternative embodiment of an expanding fusion device, or implant, is shown in FIGS. 16 and 17. FIG. 16 shows the implant in a compact configuration and FIG. 17 shows the implant in an expanded configuration. Implant 1100 includes a central shaft 1110 joined to first and second end bodies 1200, 1500. First and second intermediate bodies 1120, 1130 are disposed between the end bodies 1200, 1500. A plurality of pins 1190 connect end bodies 1200, 1500 with intermediate bodies 1120, 1130, forming joints which allow pivotal movement of the intermediate bodies relative to the end bodies. Actuation of shaft 1110 can lengthen or shorten shaft 1110 and move the implant 1100 between the compact configuration shown in FIG. 16 and the expanded configuration shown in FIG. 17, as set forth for implant 100. In the expanded configuration, the width of implant 1100 is increased, and the width increase may be greater in a first direction than in a second direction, the first and second directions perpendicular to the longitudinal axis of shaft 1110. Second intermediate body 1130 may include two arms 1600, 1700 which pivot relative to one another and to the end bodies 1200, 1500 to increase the width of the implant 1100. Bone engagement features such as ridges 1220 may be present on any bone-contacting surface of the implant. As seen in FIG. 17, the ridges 1220 may align parallel to one another in the expanded configuration of the implant 1100. The bone-contacting surface of second intermediate body 1130 may be greater than the bone-contacting surface of first intermediate body 1120. The implant 1100 may be implanted and actuated via inserter tool 1000 using methods set forth previously for implant 100. Other features set forth above in the description of implant 100 may apply to implant 1100.

It should be understood that the present system, kits, apparatuses, and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, any fusion device disclosed herein may be implanted with any of the instrumentation or methods disclosed herein. Features of one fusion device may be applied to a fusion device from another example. Features of instrumentation from one example may be applied to instrumentation from another example. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An implant for implantation between a first vertebral body and a second vertebral body, the implant comprising:
   a first end body and a second end body;
   a first intermediate body and a second intermediate body, a portion of the intermediate bodies intermediate the first and second end bodies, wherein the first intermediate body is movably joined to the first end body by a first joint, wherein the first intermediate body is movably joined to the second end body by a second joint, wherein the second intermediate body is movably joined to the first end body by a third joint, wherein the second intermediate body is movably joined to the second end body by a fourth joint;
   a shaft coupled to and extending between the first end body and the second end body, wherein the shaft is coupled to the first end body between the first and third joints, wherein the shaft is coupled to the second end body between the second and fourth joints, the implant having an implant length parallel to the shaft and an implant width perpendicular to the shaft;
   wherein the implant is transformable between a compact configuration and an expanded configuration;
   wherein in the compact configuration the end bodies are spaced apart from one another;
   wherein in the expanded configuration the end bodies are closer to one another than in the compact configuration, the implant length is shortened relative to the compact configuration, and the implant width is increased relative to the compact configuration;

wherein the increase in implant width is greater along a first direction of the implant width than along a second direction of the implant width;

wherein in the compact and expanded configurations the third and fourth joints are spaced farther apart in a direction parallel to the shaft than are the first and second joints, and the third joint is farther from the second end body in a direction parallel to the shaft than is the first joint.

2. The implant of claim 1, wherein the first direction is opposite the second direction.

3. The implant of claim 1, wherein the first and second end bodies are irregularly shaped, and the first end body is shaped as a mirror image of the second end body.

4. The implant of claim 1, wherein the first intermediate body moves at least partially along the first direction of the implant width from the shaft, wherein the second intermediate body moves at least partially along the second direction of the implant width from the shaft, and wherein the first intermediate body has a bone-contacting surface area greater than a bone-contacting surface area of the second intermediate body.

5. The implant of claim 1, further comprising an implant window between the first and second intermediate bodies, wherein the size of the implant window is increased in the expanded configuration.

6. The implant of claim 1, wherein the shaft increases and decreases in length to transform the implant between the compact configuration and the expanded configuration, wherein the implant length is equal to the shaft length in both the compact and expanded configurations.

7. The implant of claim 6, wherein the shaft comprises a screw, wherein turning the screw increases and decreases the length of the shaft.

8. The implant of claim 1, wherein the first intermediate body comprises a first arm movably joined to a second arm at an first interface, the second intermediate body comprises a third arm movably joined to a fourth arm at a second interface, wherein the first and second interfaces limit the transformation of the implant into the expanded configuration and prevent over-expansion of the implant.

9. The implant of claim 1, further comprising a spring, wherein the spring provides spring bias to urge the implant toward the expanded configuration.

10. The implant of claim 1, the implant further comprising a first bone-contacting side and a second bone-contacting side generally opposite the first bone-contacting side, an implant height measurable between the first bone-contacting side and the second bone-contacting side, the implant height perpendicular to the second bone-contacting side, wherein the implant height measured along the first direction of the implant width is greater than the implant height measured along the second direction of the implant width.

11. The implant of claim 10, wherein each of the first and second bone-contacting side comprises a plurality of bone-engagement features which project from each respective bone-contacting side.

12. The implant of claim 1, wherein the implant is implantable with a tool, the tool comprising a tool shaft having a width, and wherein the width of the implant in the compact configuration is about equal to the width of the tool shaft;

wherein the implant comprises a shoulder and the tool comprises a clamp having opposing jaws, wherein the jaws are engageable with the shoulder to grasp the implant; and wherein the tool comprises a driving feature coaxially engageable with the implant shaft, wherein the tool is actuable to transform the implant between the compact and the expanded configurations.

13. The implant of claim 1, wherein each intermediate body is pivotably joined to each end body at a joint, wherein each joint includes a pin and at least one pin hole.

14. The implant of claim 13, wherein the implant includes a transverse plane, wherein each of the intermediate bodies is movably joined at a joint, wherein the joint includes joint housing and auxiliary housing, wherein the auxiliary housing strengthens the joint housing and stabilizes the implant across the transverse plane of the implant.

15. The implant of claim 1, the implant comprising an elongated gap between each end body and each intermediate body, wherein at least a section of the elongated gap maintains substantially the same width when the implant is in the compact configuration and when the implant is in the expanded configuration.

16. A method of implanting an implant between first and second vertebral bodies, the method comprising:

inserting an implant in between the first and second vertebral bodies, the implant comprising:

a first end body and a second end body;

a first intermediate body and a second intermediate body, a portion of the intermediate bodies intermediate the first and second end bodies, wherein the first intermediate body is movably joined to the first end body by a first joint, wherein the first intermediate body is movably joined to the second end body by a second joint, wherein the second intermediate body is movably joined to the first end body by a third joint, wherein the second intermediate body is movably joined to the second end body by a fourth joint;

a shaft coupled to and extending between the first end body and the second end body, wherein the shaft is coupled to the first end body between the first and third joints, wherein the shaft is coupled to the second end body between the second and fourth joints, the implant having an implant length parallel to the shaft and an implant width perpendicular to the shaft; and transforming the implant between a compact configuration and an expanded configuration;

wherein in the compact configuration the end bodies are spaced apart from one another;

wherein in the expanded configuration the end bodies are closer to one another than in the compact configuration, the implant length is shortened relative to the compact configuration, and the implant width is increased relative to the compact configuration;

wherein the increase in implant width is greater along a first direction of the implant width than along a second direction of the implant width;

wherein in the compact and expanded configurations the third and fourth joints are spaced farther apart in a direction parallel to the shaft than are the first and second joints, and the third joint is farther from the second end body in a direction parallel to the shaft than is the first joint.

17. The method of claim 16, wherein inserting the implant between the first and second vertebral bodies further comprises inserting the implant along a lateral surgical approach.

18. The method of claim 17, wherein inserting the implant between the first and second vertebral bodies further comprises inserting the implant into the anterior third of an intervertebral disc space between the first and second vertebral bodies.

19. The method of claim 18, wherein the first direction of the implant width is a posterior direction and the second direction of the implant width is an anterior direction, wherein transforming the implant into the expanded configuration comprises increasing the implant width greater along the posterior direction than along the anterior direction.

20. The method of claim 16, further comprising mounting the implant on an tool; and actuating the tool to transform the implant from the compact configuration to the expanded configuration while the implant is between the first and second vertebral bodies.

* * * * *